(12) United States Patent  
Kostrzewski

(10) Patent No.: US 8,960,521 B2  
(45) Date of Patent: Feb. 24, 2015

(54) LOOSE STAPLES REMOVAL SYSTEM

(75) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 815 days.

(21) Appl. No.: 13/183,695

(22) Filed: Jul. 15, 2011

(65) Prior Publication Data

US 2013/0015231 A1      Jan. 17, 2013

(51) Int. Cl.
*A61B 17/072* (2006.01)
*A61B 19/02* (2006.01)

(52) U.S. Cl.
CPC ....... *A61B 17/07207* (2013.01); *A61B 19/0288* (2013.01); *A61B 2017/07264* (2013.01); *A61B 2017/07278* (2013.01)
USPC .................................. 227/176.1; 227/175.1

(58) Field of Classification Search
CPC ............... A61B 17/07207; A61B 2017/07214; A61B 17/072
USPC ...................... 227/175.1, 176.1, 178.1, 180.1; 606/219

See application file for complete search history.

(56) References Cited

U.S. PATENT DOCUMENTS

| 4,719,917 | A |   | 1/1988  | Barrows et al. |
|-----------|---|---|---------|----------------|
| 4,978,049 | A | * | 12/1990 | Green .................. 227/178.1 |
| 5,334,106 | A |   | 8/1994  | Purcell |
| 5,415,334 | A | * | 5/1995  | Williamson et al. ....... 227/178.1 |
| 2007/0057014 | A1 | * | 3/2007 | Whitman et al. ............. 227/155 |
| 2007/0073340 | A1 | * | 3/2007 | Shelton et al. ................ 606/219 |

* cited by examiner

*Primary Examiner* — Michelle Lopez
*Assistant Examiner* — Nathaniel Chukwurah

(57) ABSTRACT

A staple cartridge is provided for retaining fully formed staples not clenched through body tissue. The staple cartridge generally includes staple pockets containing surgical staples having a backspan and first and second legs projecting from the backspan and staple pushers positioned within the staple pockets beneath the surgical staples. The staple pushers include body portions having first and second flexible fingers extending from the body portions and removably engagable with the backspan of the surgical staples. The flexible fingers include flexible stems extending from the body portions and head portions extending from the flexible stems. Each head portion includes a rounded distal tip positioned offset from and outward of a central axis of the stem and an inwardly projecting grasping portion for engaging the backspan of the surgical staple. Distal ends of sidewalls of the staple pockets are flared outwardly to accommodate movement of the head portions of the flexible fingers.

15 Claims, 7 Drawing Sheets

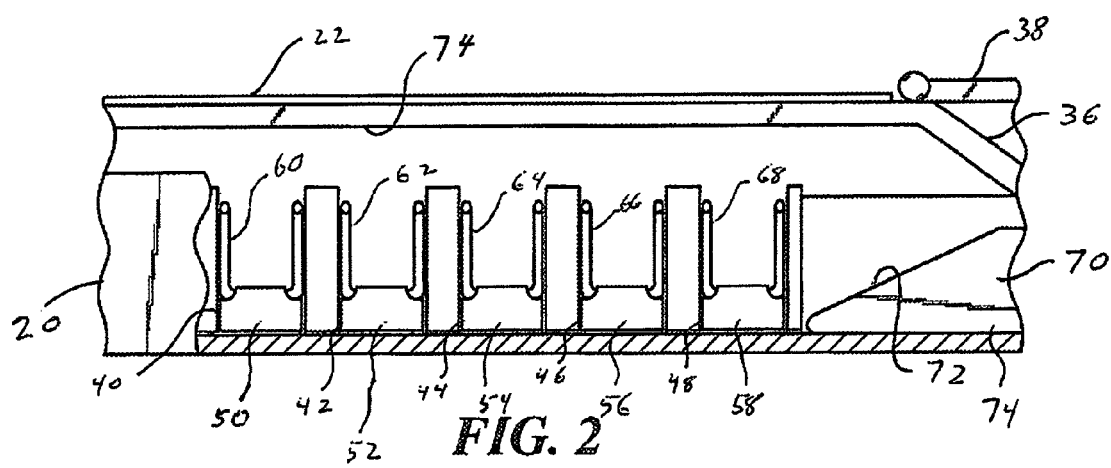
FIG. 2
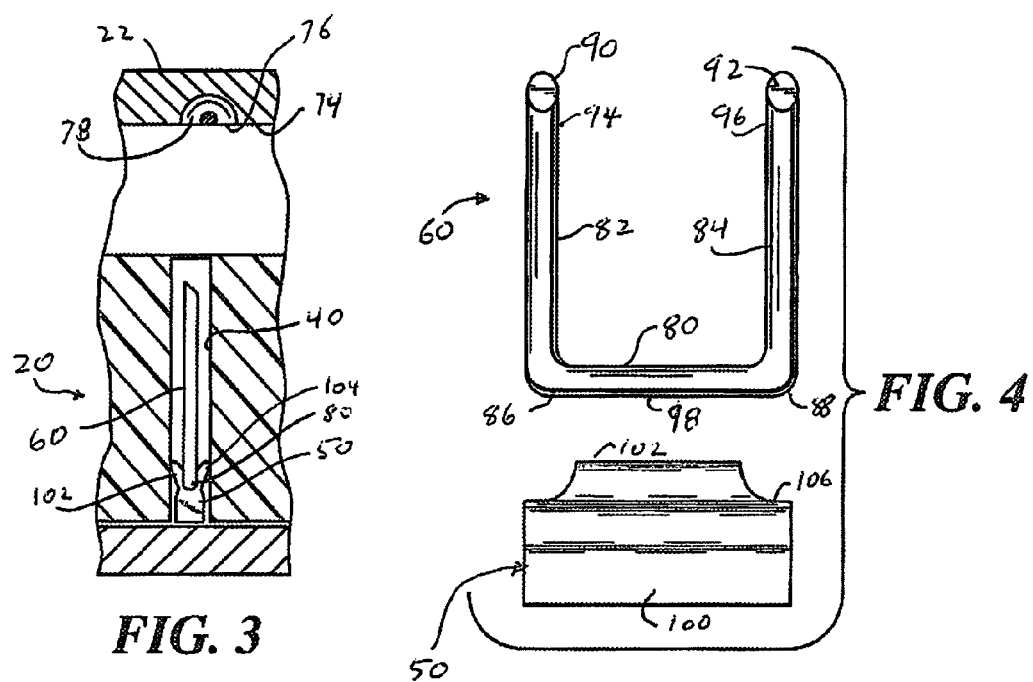
FIG. 3
FIG. 4

LOOSE STAPLES REMOVAL SYSTEM

BACKGROUND

1. Technical Field

The present disclosure relates to a system for preventing fully formed loose staples from remaining in the body of a patient. More particularly, the present disclosure relates to a staple cartridge for use with a surgical stapling instrument and having structure for retaining and removing fully formed loose staples.

2. Background of Related Art

During certain surgical procedures it is often necessary to staple body tissue in order to join tissue sections or close tubular tissue sections to prevent leakage. This is typically accomplished by the use of a surgical stapling instrument having a staple containing cartridge and an anvil member movably mounted relative to the staple cartridge. Surgical staples are retained within pockets formed in the staple cartridge and blocks or pushers are mounted beneath the staple within the staple pockets. In use, tissue is positioned between the staple cartridge and the anvil and the anvil is moved adjacent the staple cartridge to clamp the tissue therebetween. Upon actuation of the surgical stapling instrument, a drive bar movably mounted within the surgical stapling instrument passes beneath the pushers to move the pushers up within the staple pockets and sequentially eject the surgical staples out of the staple pockets. Tissue penetrating legs of the surgical staples pass through the tissue and are clinched or bent against staple clinching pockets formed in an underside of the anvil to thereby secure the staples to the tissue. Thereafter, the surgical stapling instrument is further actuated to separate the anvil from the staple cartridge thereby releasing the stapled tissue.

In some surgical procedures, the width of the tissue being stapled is less than the length of the staple cartridge and anvil, and specifically less than the length of the rows of staple containing staple pockets, resulting in surgical staples being ejected from the staple pockets and formed into the anvil without passing through tissue. Upon opening the anvil away from the staple cartridge to release the stapled tissue, these "free" or "loose" formed staples may fall away from the staple cartridge and into the body cavity of the patient where they will need to be accounted for and separately retrieved by the surgeon prior to closing the operative site. This requires not only additional time to perform the procedure but also further attention to detail at the end of the procedure to ensure that all free staples are accounted for and not left behind in the body cavity of the patient where they may cause complications.

Further, during manufacture of the staple cartridge itself, variation in tolerances between outside widths of the surgical staples and the inside widths of the staple pockets may leave the staples loosely positioned within the staple pockets. In this situation, the staples are subject to inadvertent complete or partial dislodgment out of the staple pockets during shipping and handling prior to use. This situation may make it difficult or impossible to properly use the staple cartridge with a surgical stapling instrument during a surgical procedure.

Therefore, a need exists for a staple cartridge capable of retaining staples within the staple pockets prior to use. There further exists a need for a staple cartridge which retains staples on the staple cartridge which have been formed against an associated anvil but which have not passed through tissue.

SUMMARY

There is disclosed a staple cartridge for use with a surgical stapling instrument or surgical stapler. The staple cartridge generally includes a body portion defining a staple pocket, a surgical staple disposed in the staple pocket and including a backspan and first and second legs extending from opposed ends of the backspan and a staple pusher disposed in the staple pocket. The staple pusher is removably engagable with the surgical staple. The staple pusher includes a body portion and first and second fingers extending from the body portion and engagable with the backspan of the surgical staple.

The first and second fingers are flexible relative to the body portion. Each of the first and second fingers includes a flexible stem extending from an upper surface of the body portion and a head portion extending from the flexible stem. Each of the head portions has a tip offset from axes of the associated flexible stems. The axes of the stems are central axes. The head portions further have inwardly projecting grasping projections for engagement with the backspan of the surgical staple. The body portion of the pusher includes a longitudinally extending trough for support of the backspan of the surgical staple.

In this embodiment, the staple pocket is partially defined by first and second sidewalls and distal ends of the first and second sidewalls are flared outwardly to accommodate movement of the first and second flexible fingers.

In one embodiment, the disclosed staple cartridge includes a third finger extending from the upper surface and removably engagable with the backspan of the staple.

There is also disclosed a staple pusher for use in a staple cartridge. The staple pusher includes a generally rectangular body portion having an upper surface, a first finger projecting from the upper surface. The first finger includes a first flexible stem extending from the upper surface and a first head portion extending from the stem. A second finger projects from the upper surface and includes a second flexible stem extending from the upper surface and a second head portion extending from the stem.

The first and second stems have longitudinal axes and the first and second head portions include respective first and second rounded distal tips located offset from and outward of the longitudinal axes of the first and second stems. The first and second head portions include respective first and second grasping projections extending inwardly relative to the axes of the first and second stems. In this embodiment, the upper surface of the body portion has a longitudinally extending trough for receipt of a backspan of a surgical staple.

There is still further disclosed a staple pusher for use in a staple cartridge. The staple pusher generally includes a generally rectangular body portion having an upper surface, a first finger projecting from a first side of the upper surface and a second finger projecting from a second side of the upper surface, the first and second fingers being positioned directly opposed to each other across the upper surface.

The first finger includes a first flexible stem extending from the upper surface and a first head portion extending from the stem. The first head portion additionally includes an inwardly projecting grasping projection.

In a particular embodiment, the staple pusher further includes a third finger projecting from the first side of the upper surface. In a specific embodiment, the staple pusher further includes a fourth finger projecting from the second side of the upper surface, the fourth finger positioned opposite the third finger across the upper surface.

In a more specific embodiment, the first and second fingers are longitudinally spaced from the third and fourth fingers on the upper surface of the body portion.

DESCRIPTION OF THE DRAWINGS

Various embodiments of the presently disclosed staple pushers for use in staple cartridges are disclosed herein with reference to the drawings, wherein:

FIG. 2 is an enlarged side view, partially shown in section, of a distal end of the surgical stapler incorporating one embodiment of a staple pusher within a staple cartridge;

FIG. 3 is a cross sectional view of the staple cartridge and staple pusher of FIG. 2;

FIG. 4 is an enlarged side view of the staple pusher of FIG. 2 and a surgical staple;

DETAILED DESCRIPTION OF EMBODIMENTS

Embodiments of the presently disclosed staple pushers for use in a staple cartridge of a surgical stapler will now be described in detail with reference to the drawings wherein like numerals designate identical or corresponding elements in each of the several views. As is common in the art, the term "proximal" refers to that part or component closer to the user or operator, i.e. the surgeon or physician, while the term "distal" refers to that part or component further away from the user.

Figure 1:
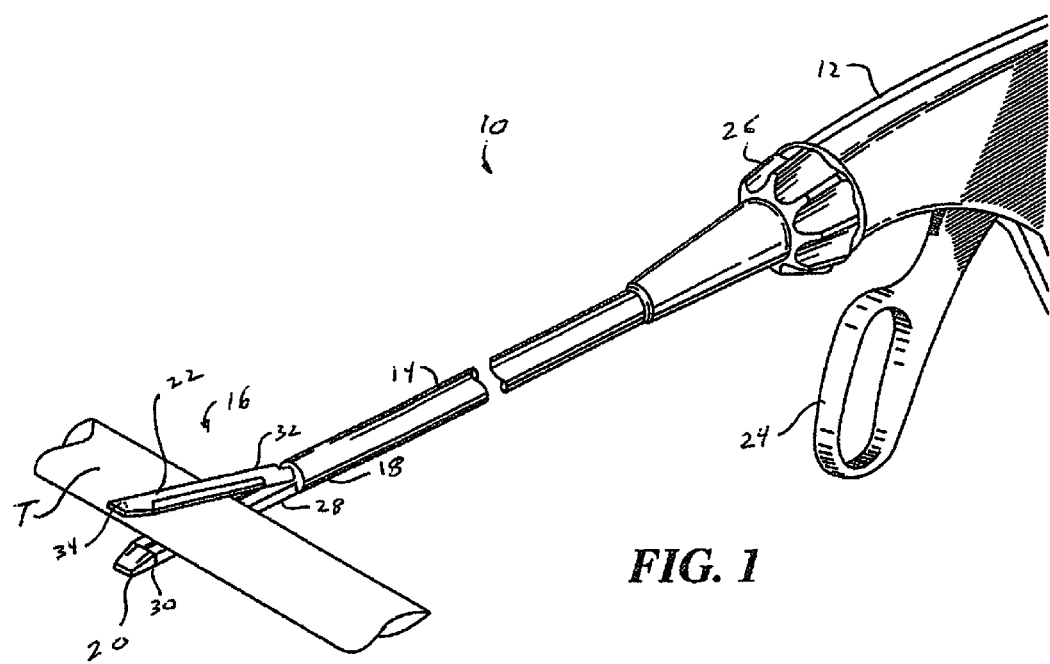
FIG. 1 is a perspective view of a surgical stapler engaging tissue.

Referring initially to FIG. 1, there is illustrated a surgical stapler 10 for use in stapling a tubular tissue T. Surgical stapler 10 generally includes a handle portion 12 having an elongate tubular member 14 extending distally from handle portion 12. An end effector 16 is affixed to a distal end 18 of elongate tubular member 14 and generally includes a staple cartridge 20, removably affixed to distal end 18, and an anvil 22 movably mounted on distal end 18 of elongate tubular member 14. A trigger 24 is provided on handle portion 12 to move anvil 22 from an open position (shown) spaced from staple cartridge 20 to a closed position (not shown) to grasp tissue T. Trigger 24 additionally actuates staple cartridge 20 in a manner described hereinbelow to staple tissue T. A rotation knob 26 is affixed to elongate tubular member 14 and is provided to rotate and orient end effector 16 relative to tissue T. As shown, when surgical stapler 10 is utilized to staple a relatively narrow tissue section, such as tissue T, tissue T lies within end effector 16 between proximal and distal ends 28 and 30 of staple cartridge 20 and proximal and distal ends 32 and 34 of anvil 22.

Referring now to FIG. 2, in order to move anvil 22 between the open and closed positions relative to staple cartridge 20, anvil 22 includes an angled proximal portion 36. Surgical stapler 10 includes a movable bar 38 which is longitudinally movable in response to actuation of trigger 24. Distal movement of movable bar 38 against angled proximal portion 36 of anvil 22 to move anvil 22 from the open position spaced from staple cartridge 20 (FIG. 1) to the closed position as shown.

Staple cartridge 20 defines a plurality of staple pockets 40, 42, 44, 46 and 48. Pushers 50, 52, 54, 56 and 58 are movably mounted within respective staple pockets 40, 42, 44, 46 and 48 and are provided to support and advance surgical staples such as, for example, surgical staples 60, 62, 64, 66 and 68 out of their respective staple pockets, through tissue and into anvil 22. A drive bar 70 is provided in surgical stapler 10 and is longitudinally mobile in response to actuation of trigger 24. Drive bar 70 includes an angled distal tip 72 which sequentially passes under, and vertically moves, pushers 58, 56, 54, 52 and 50 to drive surgical staples 68, 66, 64, 62 and 60 out of respective staple pockets 48, 46, 44, 42 and 40 and into a staple clinching undersurface 74 of anvil 22.

Referring for the moment to FIG. 3, anvil 22 is provided with a plurality of staple clinching pocket pairs 76, 78 etc. formed in undersurface 74 of anvil 22. Staple clinching pockets 78 are provided to receive tips of surgical staples such as, for example, surgical staple 60, and bend or clinch the tips of surgical staple 60 about tissue in a manner described in more detail hereinbelow. It should be noted that while the following discussion of the disclosed staple pushers and surgical staples are described with respect to staple pusher 50 and surgical staple 60, the remaining staple pushers 52, 54, 56 and 58 and associated surgical staples 62, 64, 66 and 68 are substantially identical thereto.

Referring now to FIG. 4, surgical staple 60 generally includes a backspan 80 and first and second legs 82 and 84 extending from opposed end 86 and 88 of backspan 80. Angled tissue penetrating tips 90 and 92 are provided on distal ends 94 and 96 of first and second legs 82 and 84 to facilitate piercing of first and second legs 82 and 84 through tissue. Backspan 80 includes a central portion 98 located between opposed ends 86 and 88. Staple pusher 50 includes a body portion 100 having first and second flexible fingers 102 and 104 (FIG. 5) extending from an upper surface 106 of body portion 100. First and second flexible fingers 102 and 104 are configured to releasably engage central portion 98 of backspan 80 of surgical staple 60.

Figure 5:
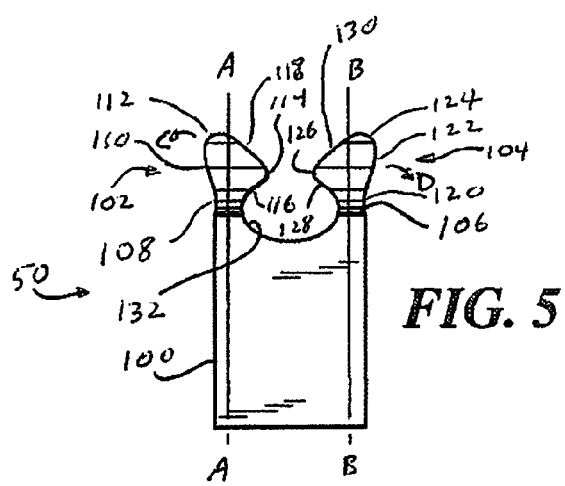
FIG. 5 is an end view of the staple pusher of FIG. 2.

Referring now to FIG. 5, in order to grasp backspan 80 of surgical staple 60, first flexible finger 102 includes a flexible stem 108 extending from upper surface 106 of body portion 100. A head portion 110 extends from flexible stem 108 and generally includes a tissue engaging rounded distal tip 112 and an inwardly extending grasping projection 114 for releasably securing back span 80 of surgical staple 60 between first and second flexible fingers 102 and 104. Head portion 110 includes an undersurface 116 which engages central portion 98 of backspan 80 of surgical staple 60 and an angled face 118 which extends between rounded distal tip 112 and grasping projection 114. Angled face 118 rides along the surface of tissue engaged by head portion 110 to splay away from backspan 80 and release fully formed surgical staple 60 from pusher 50 in a manner described in more detail hereinbelow.

Likewise, second flexible finger 104 generally includes a flexible stem 120 extending from upper surface 106 of body portion 100 and terminates in a head portion 122. Head portion 122 generally includes a rounded distal tip 124 and an inwardly extending grasping projection 126. An undersurface 128 of head portion 122 engages backspan 80 of surgical staple 60 while an angled face 130 extends between rounded distal tip 124 and grasping projection 126 to engage tissue and facilitate splaying grasping projection 126 away from backspan 80 to release surgical staple 60 from pusher 50 in response to engagement with tissue.

In order to release surgical staple 60 from grasping projections 114 and 126 of head portions 110 and 122, rounded distal tips 112 and 124 are located offset from and outward of respective central axes A-A and B-B extending through stems 108 and 120 of first and second flexible fingers 102 and 104. Thus, as rounded distal tips 112 and 124 are urged against tissue, head portions 110 and 122 are rotated or urged outward of axes A-A and B-B in the direction of arrows C and D thereby pulling respective grasping projections 114 and 126 away from engagement with backspan 80 of surgical staple 60.

Figure 6:
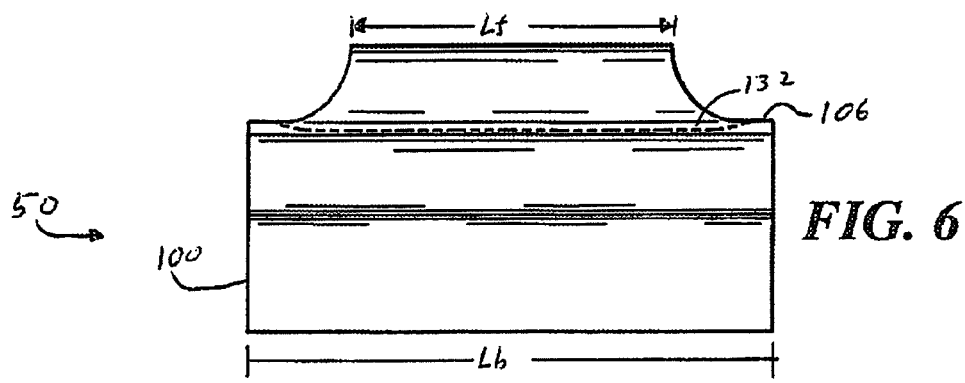
FIG. 6 is a side view of the staple pusher of FIG. 2.

Referring to FIG. 6, the lengths Lf of first and second flexible fingers 102 and 104 are substantially less than the length Lb of rectangular body portion 100. This ensures that flexible fingers 102 and 104 only engage central portion 98 back span 80 of surgical staple 60 and do not interfere with the bending of opposed ends 86 and 88 as surgical staple 60 is formed through tissue and against anvil 22.

Figure 7:
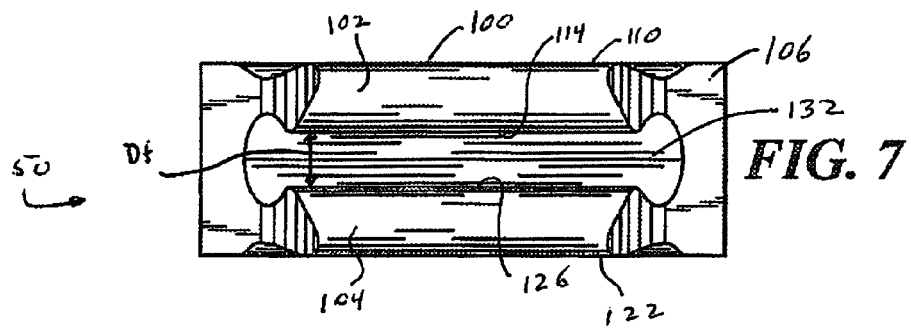
FIG. 7 is a top view of the staple pusher of FIG. 2.

As best shown in FIGS. 5-7, in order to better support backspan 80 of surgical staple 60, upper surface 106 of body portion 100 of pusher 50 is formed with a partial longitudinally extending trough 132 for receipt of central portion 98 of backspan 80. As best shown in FIGS. 5 and 7, grasping projections 114 and 126 of respective head portions 110 and 122 of first and second flexible fingers 102 and 104 project inwardly across and over trough 132. This allows grasping projections 114 and 126 to prevent release of surgical staple 60 from pusher 50 until surgical staple 60 has been fully formed through tissue in a manner described hereinbelow. With specific reference to FIG. 7, the distance Df between grasping projections 114 and 126 of head portions 110 and 122 of first and second flexible fingers 102 and 104 is less than the diameter Db of backspan 80 (FIG. 8) to prevent premature release of surgical staple 60.

Figure 8:
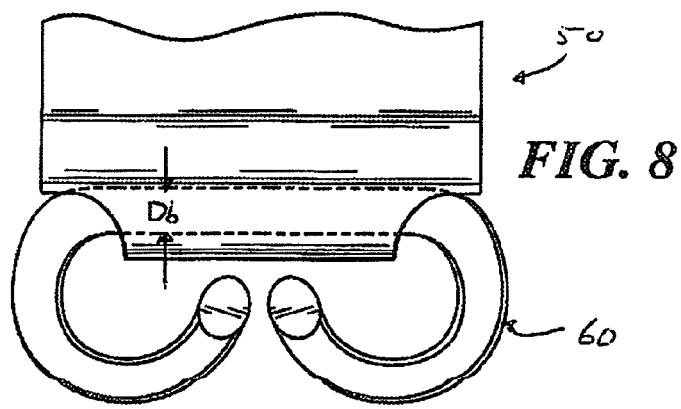
FIG. 8 is a side view of the staple pusher of FIG. 2 retaining a fully formed surgical staple.

In the event that rounded distal tips 112 and 124 of first and second flexible fingers 102 and 104 do not engage tissue during actuation the surgical stapler 10, the fully formed surgical staple, such as surgical staple 60, will be retained by pusher 50 and not released into the body cavity as illustrated in FIG. 8.

Referring to FIGS. 9-12, there is disclosed an alternative embodiment of a staple pusher 140 for use with surgical stapler 10. Similar to staple pusher 50 described herein above, staple pusher 140 generally includes a body portion 142 having first and second flexible opposed fingers 144 and 146 extending from an upper surface 148 of body portion 142. First and second flexible fingers 144 and 146 includes respective stems 150 and 152 extending from upper surface 148 and head portions 154 and 156 extending from stems 150 and 152. Head portion 154 generally includes a rounded distal tip 158 and a grasping projection 160. An undersurface 162 of grasping projection 160 engages a backspan of a surgical staple such as, for example, backspan 80 of surgical staple 60, and an angled face 164 extending between rounded distal tip 158 and grasping projection 160 engages tissue to splay or rotate head portion 154 away from backspan 80 of surgical staple 60. Likewise, head portion 156 includes a rounded distal tip 166 and a grasping projection 168. An undersurface 170 of grasping projection 168 engages backspan 80 of surgical staple 60 and an angled face 172 extends between rounded distal tip 166 and grasping projection 168 for engagement with tissue. Similar to head portions 110 and 122 of staple pusher 50 described herein above, rounded distal tips 158 and 166 of first and second flexible fingers 144 and 146 are offset from and outward of respective axes E-E and F-F extending through stems 150 and 152. Thus, as rounded distal tips 158 and 166 engage tissue, head portions 110 and 122 are rotated outward to release a backspan of a surgical staple from grasping projections 160 and 168.

Figure 9:
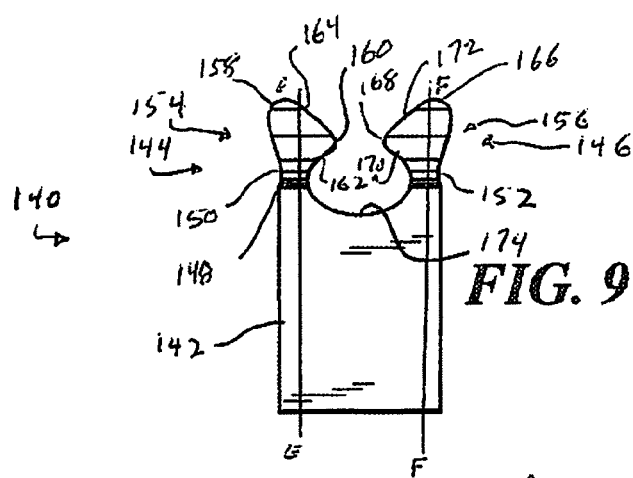
FIG. 9 is an end view of an alternative embodiment of a staple pusher.
Figure 10:
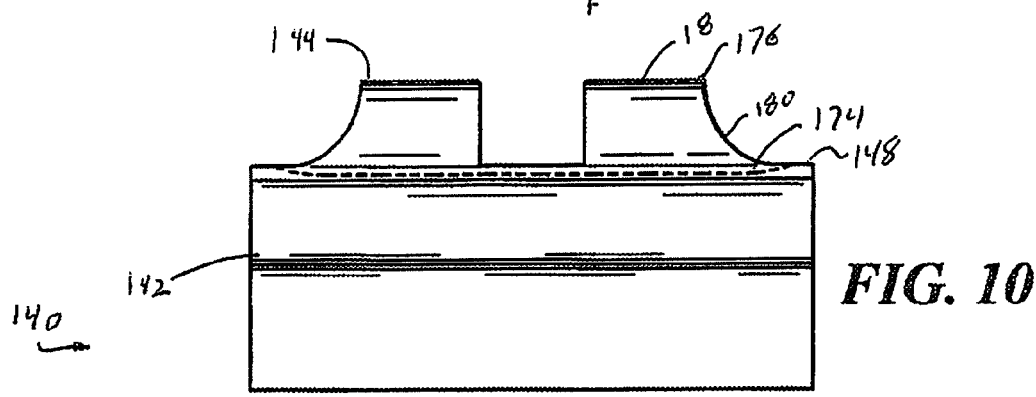
FIG. 10 is a side view of the staple pusher of FIG. 9
Figure 11:
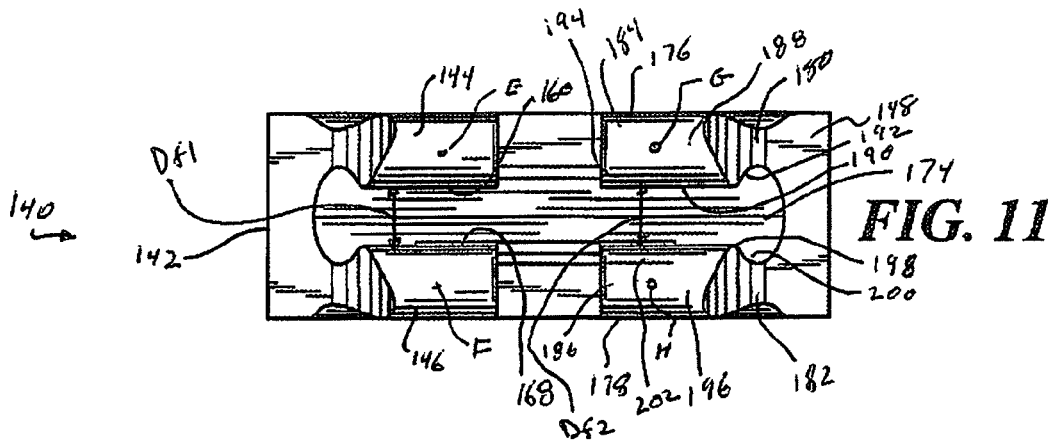
FIG. 11 is a top view of the staple pusher of FIG. 9.
Figure 12:
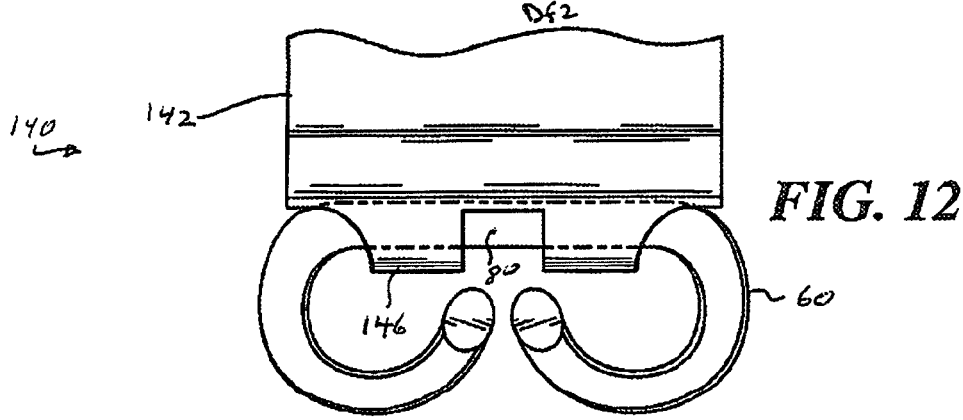
FIG. 12 is a side view of the staple pusher of FIG. 9 retaining a fully formed surgical staple.

With reference to FIGS. 9-11, and similar to pusher 50 described herein above, in order to better support backspan 80 of surgical staple 60, upper surface 148 of body portion 142 of pusher 140 is formed with a partial longitudinally extending trough 174 for receipt of central portion 98 of backspan 80. As best shown in FIGS. 9 and 11, grasping projections 160 and 168 of respective head portions 154 and 156 of first and second flexible fingers 144 and 146 project inwardly across and over trough 174 allowing grasping projections 160 and 168 to prevent release of surgical staple 60 from pusher 140 until surgical staple 60 has been fully formed through tissue in a manner described hereinbelow.

With specific reference to FIG. 11, pusher 140 is further provided with opposed third and fourth flexible fingers 176 and 178. Third and fourth fingers 176 and 178 are longitudinally space from first and second fingers 144 and 146, respectively, along body portion 142. Third and fourth fingers 176 and 178 are substantially similar to first and second fingers 144 and 146. Third and fourth flexible fingers 176 and 178 generally include respective flexible stems 180 and 182 extending from opposed side of upper surface 148 of body portion 142 and respective head portions 184 and 186 extending from stems 180 and 182. Head portion 184 includes a rounded distal tip 188 and a grasping projection 190. An undersurface 192 of grasping projection 190 is configured to engage backspan 80 of surgical staple 60 and an angled face 194 extending between grasping projection 190 and rounded distal tip 188 is provided for engaging tissue. Likewise, head portion 186 includes a rounded distal tip 196 and a grasping projection 198 having an undersurface 200 for engaging backspan 80 of surgical staple 60. An angled face 202 extends between grasping projection 198 and rounded distal tip 196 for engaging tissue. Similar to the flexible fingers described hereinabove, rounded distal tips 188 and 196 of third and fourth flexible fingers 176 and 178 are offset from and outward of respective axes G and H extending centrally through stems 180 and 182 to allow third and fourth flexible fingers to splay outwardly upon engagement with tissue.

In this embodiment, the addition of two extra flexible fingers, i.e., third and fourth flexible fingers 176 and 178 allows stems 150, 152, 180 and 182 of first, second, third and fourth flexible fingers 144, 146 176 and 178, respectively, to be formed from a weaker material or be relatively more flexible in order to facilitate easier bending upon engagement with tissue while still maintaining sufficient holding pressure on backspan 80 of surgical staple 60.

Similar to pusher 50 described herein above, the distance Df1 between grasping projections 160 and 168 of first and second flexible fingers 144 and 146 is less than the diameter Db of backspan 80 of surgical staple 60. Likewise, the distance Df2 between grasping projections 190 and 198 of third and fourth flexible fingers 176 and 178 is less than the distance Db of backspan 80 of surgical staple 60 (FIG. 12) to prevent inadvertent release of surgical staple 60 from pusher 140 prior to engagement with tissue.

Referring now to FIGS. 1, 3 and 13-16, the use of pusher 50 within staple cartridge 20 of surgical stapling instrument 10 to retain a fully formed surgical staple such as, for example, surgical staple 60, in the absence of tissue will now be described. Referring initially to FIG. 1, surgical stapler 10 is positioned adjacent tissue such that a tubular tissue section T is positioned between staple cartridge 20 and anvil 22. As best shown in FIG. 3, backspan 80 of surgical staple 60 is firmly grasped between first and second flexible fingers 102 and 104 of pusher 50 in a manner described herein above. Additionally, it can be seen that the abutment of first and second flexible fingers 102 and 104 against inner walls 204 and 206 of staple pocket 40 assists in maintaining first and second flexible fingers 102 and 104 in engagement with backspan 80.

Surgical stapler 10 is then actuated via movement of trigger 24 to bring anvil 22 to the closed position relative to staple cartridge 20 thereby grasping tissue section T therebetween.

Figure 13:
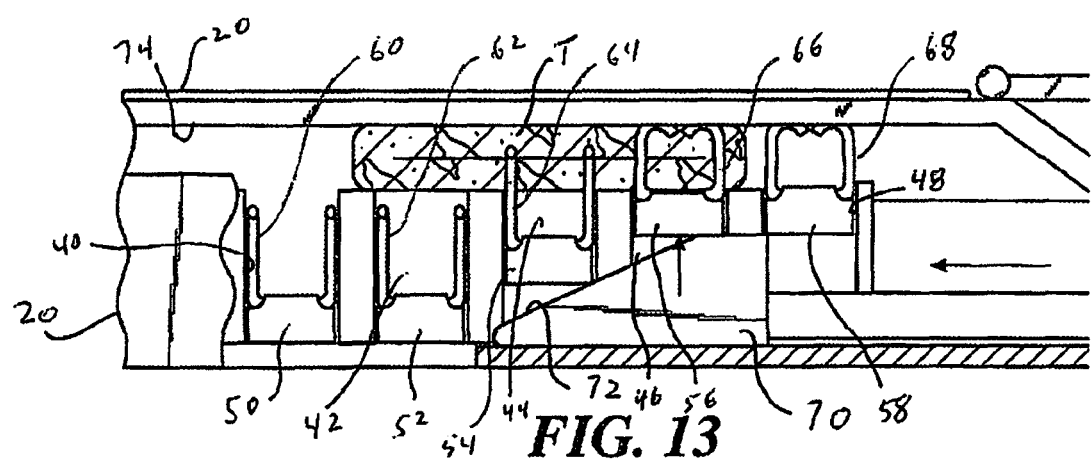
FIG. 13 is side view similar to FIG. 2 illustrating initial engagement of a drive bar with the staple pushers to drive the surgical staples through tissue and into an anvil of the staple cartridge.

Referring now to FIG. 13, as trigger 24 (FIG. 1) is actuated, drive bar 70 advances distally through staple cartridge 20 such that angled distal tip 72 passes beneath pushers 58, 56, 54, 52 and 50 to drive staples 68, 66, 64, 62 and 60 out of staple pockets 48, 46, 44, 42 and 40 and into undersurface 74 of anvil 20 where they are crimped closed. Some of the staples, such as, staple 66, 64 and 62 pass through tissue T and are crimped closed against undersurface 74 of anvil 22 thereby staple tissue T. The remaining staples, such as staples 60 and 68 are ejected out of staple pocket 40 and 48 which lie outside the width of tissue T and are also crimped closed against undersurface 74 of anvil 20.

Figure 14:
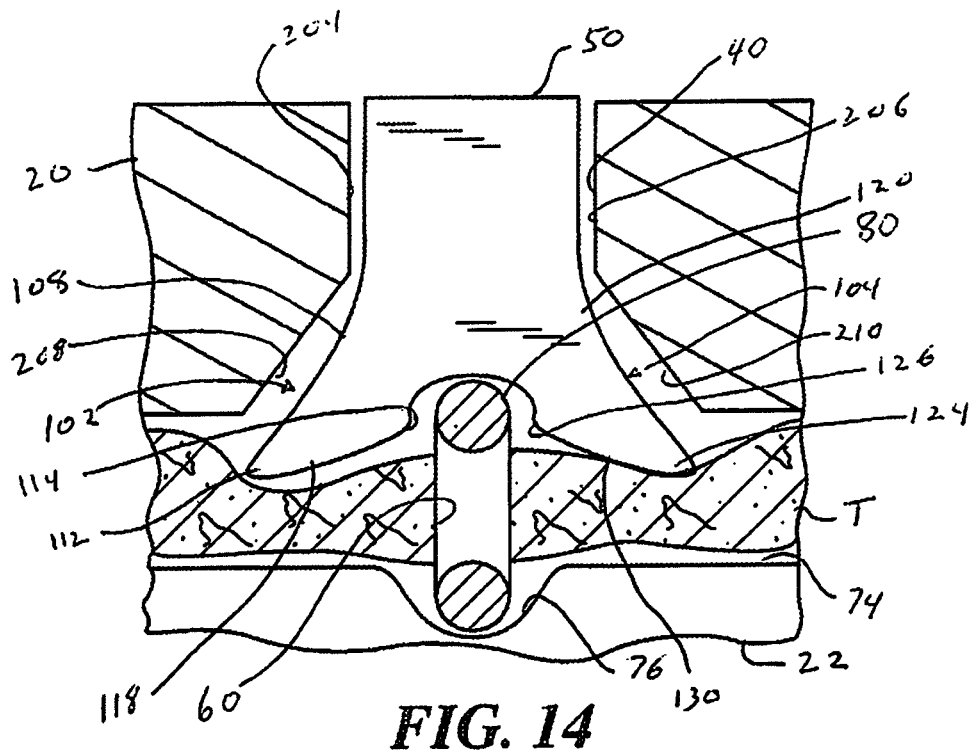
FIG. 14 is a cross sectional view illustrating the engagement of the staple pusher with tissue to release the surgical staple from the staple pusher.

Referring specifically to FIG. 14, pusher 50 is illustrated in operation in a situation where surgical staple 60 passes through tissue T. It should be noted that, while the following description of the operation of pusher 50 is being described herein in use where surgical staple 60 engages tissue T and where surgical staple 60 does not engage tissue (FIG. 15), the operation of the remaining staple pushers such as, for example, pushers 52, 54, 56 and 58 function substantially identically to retain or release associated surgical staples 62, 64, 66 and 68.

As staple pusher 50 is advanced within staple pocket 40 to eject surgical staple 60 through tissue T, rounded distal tips 112 and 124 of first and second flexible fingers 102 and 104 initially engage tissue T and are splayed outwardly or rotated away from backspan 80 due to the flexibility of stems 108 and 120. Thereafter, angled faces 118 and 130 of first and second flexible fingers 102 and 104 continue to engage and ride along tissue T to further flex and splay outwardly first and second flexible fingers 102 and 104. This flexion draws grasping projections 114 and 126 away from backspan 80 of surgical staple 62 thereby releasing surgical staple 60 from pusher 50. As shown, in order to facilitate outward movement of first and second flexible fingers 102 and 104 away from backspan 80 of surgical staple 60, inner walls 204 and 206 of staple pocket 40 are formed with flared distal ends 208 and 210 to provide additional clearance for movement of first and second flexible fingers 102 and 104.

Figure 15:
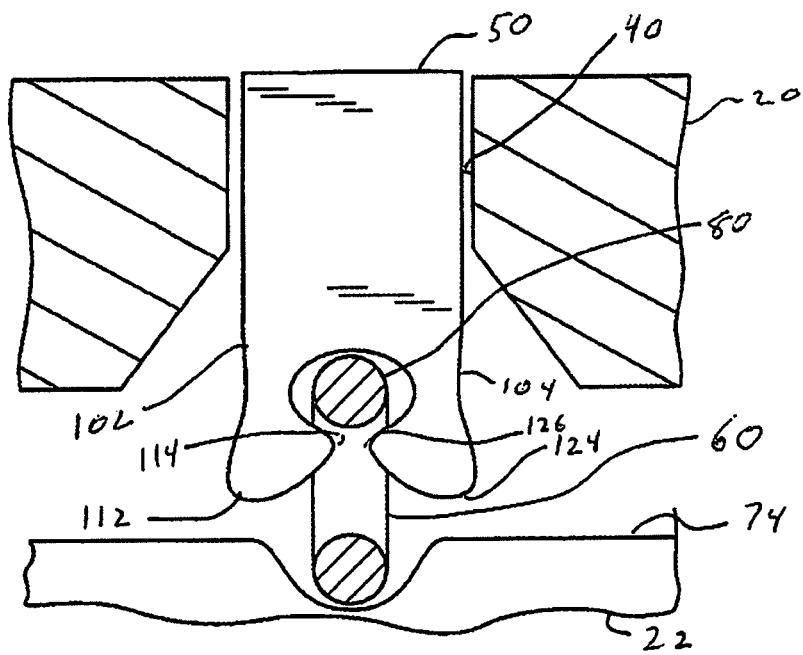
FIG. 15 is a view similar to FIG. 14 in the absence of tissue illustrating continued engagement of the staple pusher with the surgical staple.

Referring now to FIG. 15, in a situation where tissue T does not overlie staple pocket 40, pusher 50 still advances surgical staple 60 out of staple pocket 40 and into engagement with undersurface 74 of anvil 22 thereby crimp surgical staple 60. However, in this situation, rounded distal tips 112 and 124 of first and second flexible fingers 102 and 104 do not engage tissue and are thus not splayed outwardly and therefore do not release backspan 80 of surgical staple 60 from grasping projections 114 and 126 of first and second flexible legs 102 and 104 respectively. As shown, in the absence of tissue, pusher 50 securely retains fully formed and crimped staple 60.

Figure 16:
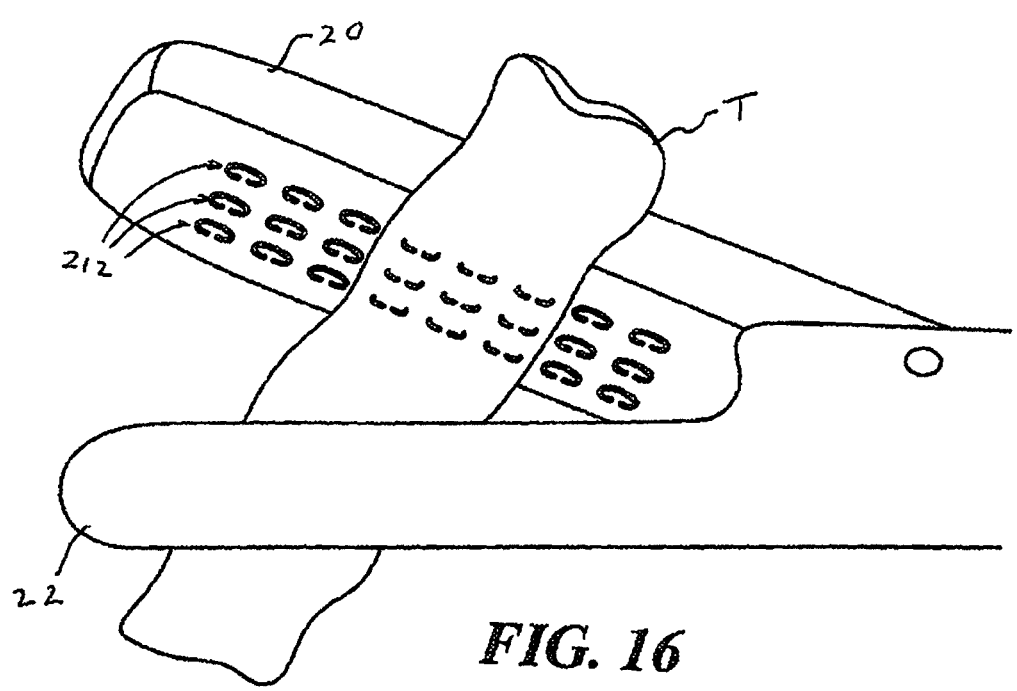
FIG. 16 is a perspective view of the distal end of the surgical stapler with the anvil open relative to the staple cartridge and fully formed staples, not passing through tissue, retained within the staple cartridge.

As best shown in FIG. 16, upon opening anvil 22 away from staple cartridge 20 to thereby release the now stapled tissue T, staples which have not passed through tissue such as, for example, rows of staples 212 are securely retained within staple cartridge 20 by the pushers disclosed herein and therefore prevented from falling free into the body cavity of the patient.

It will be understood that various modifications may be made to the embodiments disclosed herein. For example, while the flexible fingers are illustrated as being positioned directly opposite each other on the respective body portion of the pusher, the flexible fingers may be staggered relative to the opposed fingers. Further, opposed fingers need not both include grasping projections but a grasping projection may be provided only on a single opposed finger of a pair of opposed fingers. Additionally, pushers incorporating both single and multiple pairs of opposed fingers may be utilized within a single staple cartridge to better accommodate various thicknesses and toughness is of tissue encountered. Therefore, the above description should not be construed as limiting, but merely as exemplifications of particular embodiments. Those skilled in the art will envision other modifications within the scope and spirit of the claims appended hereto.

the invention claimed is:

1. A staple cartridge for use with a surgical stapling instrument comprising:
   a staple pocket;
   a surgical staple disposed in the staple pocket, the surgical staple including a backspan and first and second legs extending from opposed ends of the backspan; and
   a staple pusher disposed in the staple pocket and being removably engageable with the surgical staple, the staple pusher including a body portion having first and second fingers extending from the body portion and engageable with the backspan of the surgical staple, wherein the first finger is flexibly coupled to an upper surface of the body portion by a flexible stem such that the first finger is movable generally transverse to a longitudinal axis of the staple pusher.

2. The staple cartridge as recited in claim 1, wherein the a head portion extends longitudinally away from the stem.

3. The staple cartridge as recited in claim 2, wherein the head portion has a tip offset from an axis of the stem.

4. The staple cartridge as recited in claim 3, wherein the axis of the stem is a central axis.

5. The staple cartridge as recited in claim 3, wherein the head portion has an inwardly projecting grasping projection for engagement with the backspan of the surgical staple.

6. The staple cartridge as recited in claim 2, wherein the upper surface of the body portion includes a longitudinally extending trough for support of the backspan of the surgical staple.

7. The staple cartridge as recited in claim 2, further comprising a third finger extending from the upper surface and removably engageable with the backspan of the staple.

8. The staple cartridge as recited in claim 1, wherein the staple pocket is partially defined by first and second sidewalls and distal ends of the first and second sidewalls are flared outwardly.

9. A staple pusher for use in a staple cartridge comprising:
   a generally rectangular body portion having an upper surface;
   a first finger projecting from the upper surface, the first finger including a first flexible stem extending from the upper surface and a first head portion extending from the stem; and
   a second finger projecting from the upper surface, the second finger including a second flexible stem extending from the upper surface and a second head portion extending from the stem, wherein the first and second head portions include respective first and second grasping projections extending inwardly relative to an axis of the first and second stems.

10. The staple pusher as recited in claim 9, wherein the first and second stems have a longitudinal axis and the first and second head portions include respective first and second rounded distal tips located offset from and outward of the longitudinal axis of the first and second stems.

11. The staple pusher as recited in claim 9, wherein the upper surface of the body portion has a longitudinally extending trough for receipt of a backspan of a surgical staple.

12. A staple pusher for use in a staple cartridge comprising:
 a generally rectangular body portion having an upper surface;
 a first finger projecting from a first side of the upper surface; and
 a second finger projecting from a second side of the upper surface, the first and second fingers being positioned directly opposed to each other across the upper surface, wherein the first finger includes a first flexible stem extending from the upper surface and a first head portion extending from the stem, the first head portion including an inwardly projecting grasping projection.

13. The staple pusher as recited in claim 12, further comprising a third finger projecting from the first side of the upper surface.

14. The staple pusher as recited in claim 13, further comprising a fourth finger projecting from the second side of the upper surface, the fourth finger positioned opposite the third finger across the upper surface.

15. The staple pusher as recited in claim 14, wherein the first and second fingers are longitudinally spaced from the third and fourth fingers on the upper surface of the body portion.

* * * * *